US 6,632,210 B1

(12) United States Patent
Glasgow et al.

(10) Patent No.: US 6,632,210 B1
(45) Date of Patent: Oct. 14, 2003

(54) SANITARY NAPKIN WITH INTERGLUTEAL STRIP

(75) Inventors: Tara Glasgow, New Hope, PA (US); James P. Barr, East Amwell, NJ (US); Carol B. Gell, Belle Mead, NJ (US); Robert Rial, Cranford, NJ (US); Safiyya Shabazz-Houston, Philadelphia, PA (US); Joseph Luizzi, Newtown, PA (US); Lai Hing Louie, Kendall Park, NJ (US); Pramod S. Mavinkurve, Princeton, NJ (US)

(73) Assignee: Neil-PPC, Inc., Skillman, NJ (US)

( * ) Notice: Subject to any disclaimer, the term of this patent is extended or adjusted under 35 U.S.C. 154(b) by 160 days.

(21) Appl. No.: 09/747,208

(22) Filed: Dec. 22, 2000

(51) Int. Cl.$^7$ .................................. A61F 13/15
(52) U.S. Cl. ..................... 604/385.17; 604/385.04; 604/385.03; 604/385.05; 604/385.01
(58) Field of Search .................... 604/317–402; 2/267, 268, 400

(56) References Cited

U.S. PATENT DOCUMENTS

| 2,742,903 A | | 4/1956 | Lightner |
|---|---|---|---|
| RE24,385 E | | 10/1957 | Flanders |
| D191,649 S | | 10/1961 | Dudley |
| 3,183,909 A | * | 5/1965 | Roehr |
| D215,386 S | | 9/1969 | Glassman |
| D234,162 S | | 1/1975 | Andersen |
| D236,385 S | | 8/1975 | Celander et al. |
| 3,906,952 A | | 9/1975 | Zamist |
| D240,562 S | | 7/1976 | Whitehead et al. |
| D240,563 S | | 7/1976 | Whitehead et al. |
| D240,564 S | | 7/1976 | Whitehead et al. |
| D247,368 S | | 2/1978 | Whitehead |
| 4,072,151 A | | 2/1978 | Levine |
| 4,184,498 A | | 1/1980 | Franco |
| 4,484,919 A | | 11/1984 | Sohn et al. |
| 4,533,357 A | | 8/1985 | Hall |
| 4,556,146 A | | 12/1985 | Swanson et al. |
| 4,596,570 A | | 6/1986 | Jackson et al. |
| 4,687,478 A | | 8/1987 | Van Tilburg |
| 4,753,648 A | | 6/1988 | Jackson |
| 4,900,319 A | | 2/1990 | Richwine |
| 4,950,264 A | | 8/1990 | Osborn, III |
| 4,964,860 A | | 10/1990 | Gipson et al. |
| 5,009,653 A | | 4/1991 | Osborn, III |
| 5,100,399 A | | 3/1992 | Janson et al. |
| 5,106,385 A | | 4/1992 | Allen et al. |
| 5,261,901 A | | 11/1993 | Guay |
| 5,267,992 A | | 12/1993 | Van Tilburg |
| 5,295,986 A | | 3/1994 | Zehner et al. |
| 5,305,162 A | | 4/1994 | Kushiro et al. |

(List continued on next page.)

FOREIGN PATENT DOCUMENTS

| CH | 643730 A | | 6/1984 |
|---|---|---|---|
| DE | 298 08 968 A | | 9/1998 |
| DE | 299 15 071 U1 | | 1/2000 |
| EP | 0 164 595 A1 | | 12/1985 |
| JP | 79 117473 | | 5/1997 |
| WO | WO 90/04956 | * | 5/1990 |
| WO | WO 90/04956 A1 | | 5/1990 |
| WO | WO 97/01997 A1 | | 1/1997 |

(List continued on next page.)

OTHER PUBLICATIONS

Eureopean Search Report for Application No. 02002564.9–1217 dated May 29, 2002.

*Primary Examiner*—Jeanette Chapman
(74) *Attorney, Agent, or Firm*—James P. Barr

(57) ABSTRACT

A sanitary napkin has a strip that extends rearwardly to reside in the intergluteal crevice. The pad fits snugly against the body without penetrating. Because the strip provides improved body contact, similar protection is achieved with a smaller pad, thus providing a discretion benefit to the wearer.

19 Claims, 10 Drawing Sheets

U.S. PATENT DOCUMENTS

| | | | |
|---|---|---|---|
| 5,374,262 A | | 12/1994 | Keuhn, Jr. et al. |
| 5,383,868 A | * | 1/1995 | Hym ..................... 604/385.1 |
| 5,445,628 A | | 8/1995 | Gipson et al. |
| D366,524 S | | 1/1996 | Chung |
| 5,489,282 A | | 2/1996 | Zehner et al. |
| 5,520,675 A | * | 5/1996 | Knox-Sigh ............. 604/385.01 |
| 5,683,373 A | | 11/1997 | Darby |
| 5,713,886 A | * | 2/1998 | Sturino ..................... 604/390 |
| D392,736 S | | 3/1998 | Erickson |
| 5,729,835 A | | 3/1998 | Williams |
| D394,503 S | | 5/1998 | Perrini |
| D395,504 S | | 6/1998 | Darby |
| D395,508 S | | 6/1998 | Darby |
| 5,772,649 A | | 6/1998 | Siudzinski |
| 5,843,267 A | | 12/1998 | Cashaw et al. |
| 5,846,232 A | | 12/1998 | Serbiak et al. |
| D411,006 S | | 6/1999 | Nixon et al. |
| 6,100,442 A | * | 8/2000 | Samuelsson et al. ....... 604/378 |
| 6,198,019 B1 | * | 3/2001 | Hansson et al. ............ 604/378 |
| 6,293,931 B1 | * | 9/2001 | Romare .................. 604/385.01 |
| 6,348,047 B1 | * | 2/2002 | Harper .................. 604/385.17 |
| 6,350,257 B1 | * | 2/2002 | Bjorklund et al. ..... 604/385.01 |
| 6,350,258 B1 | * | 2/2002 | Markowiecki ....... 604/385.201 |

FOREIGN PATENT DOCUMENTS

| | | |
|---|---|---|
| WO | WO 97/03623 A2 | 2/1997 |
| WO | WO 98/51249 A1 | 11/1998 |
| WO | 01 358 87 A1 | 5/2001 |
| WO | 01 358 91 A1 | 5/2001 |
| WO | 01 49232 A1 | 7/2001 |

* cited by examiner

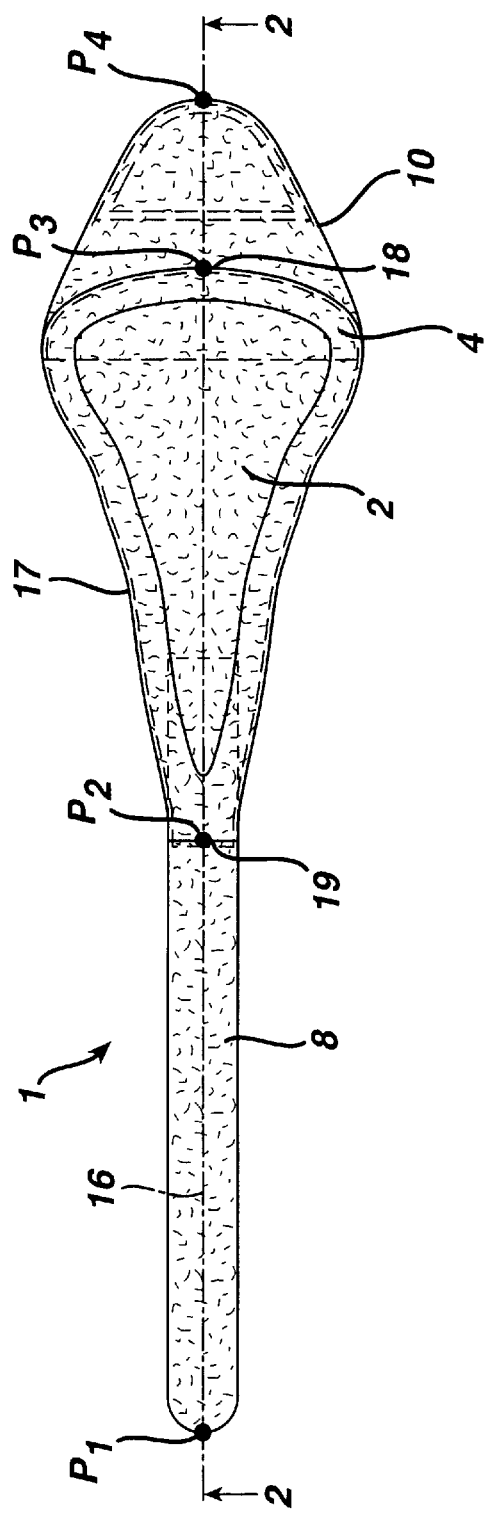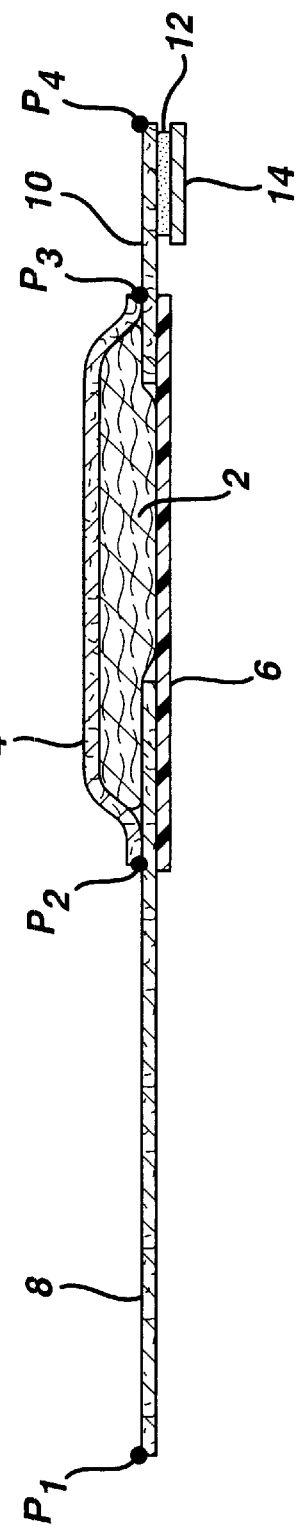

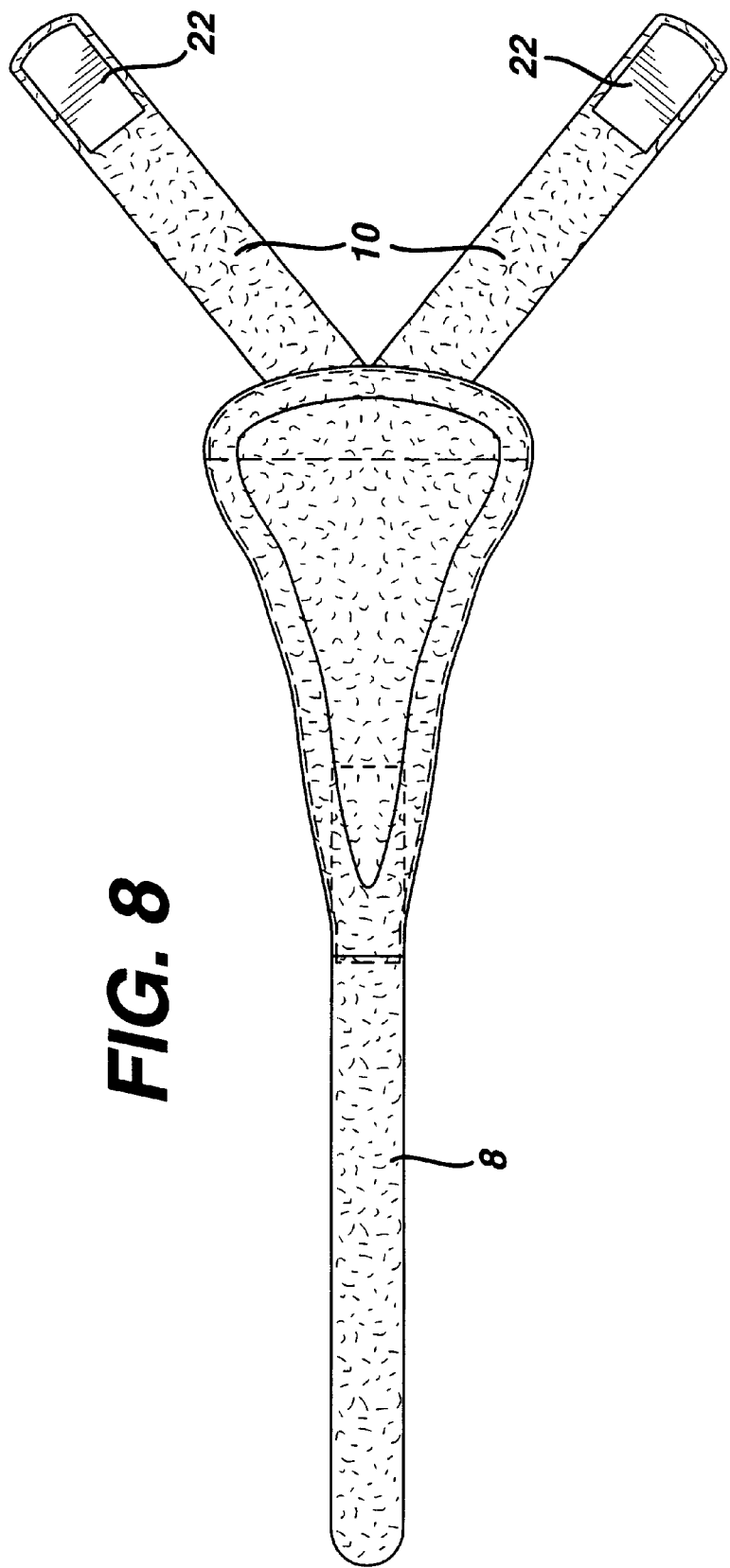

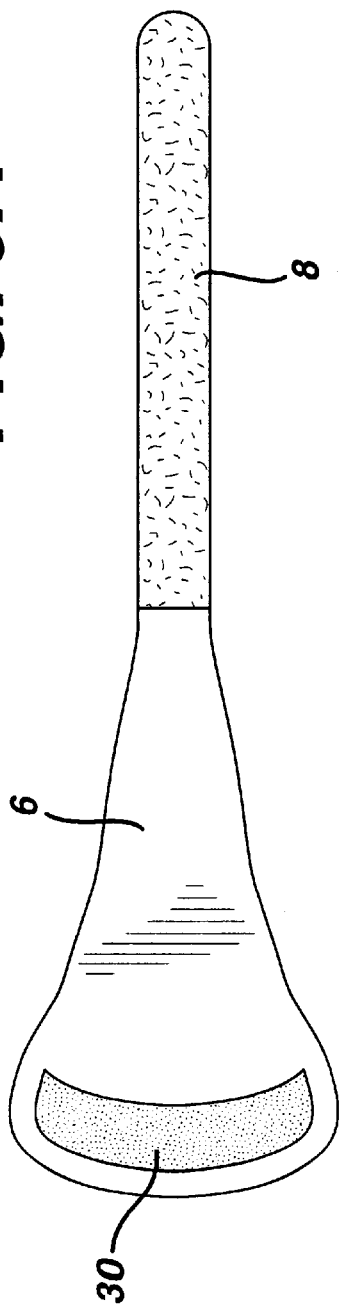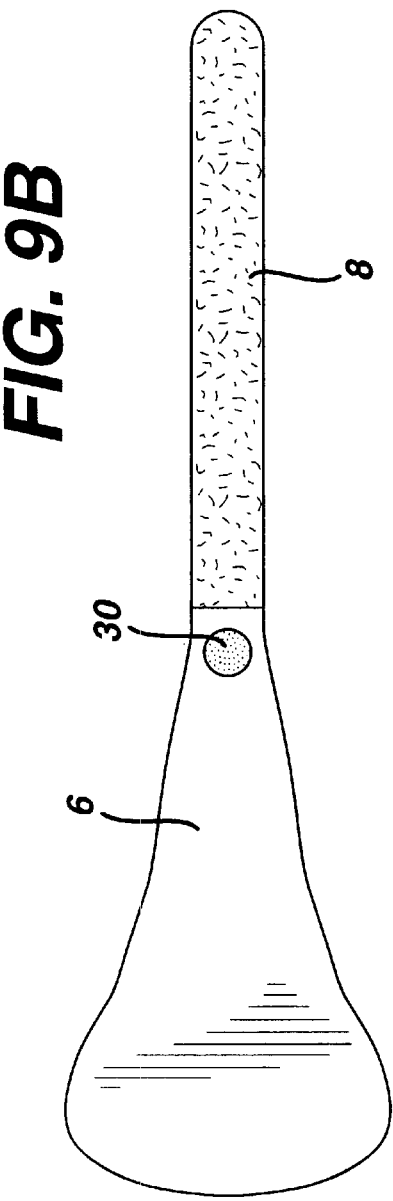

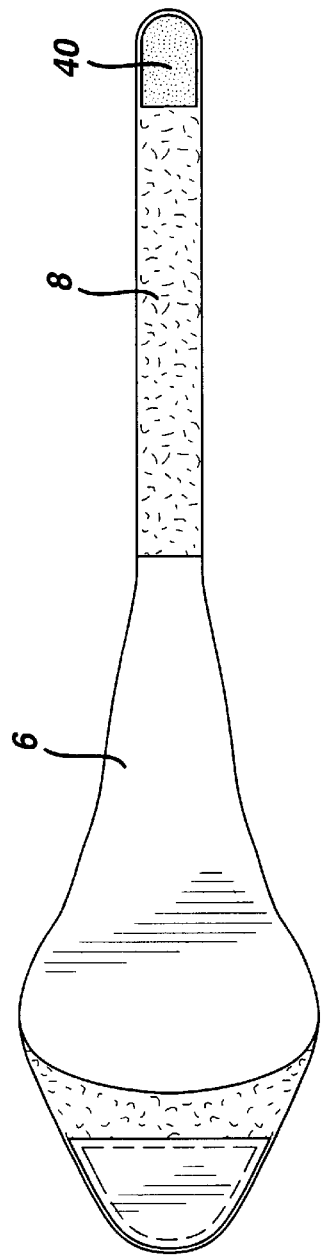
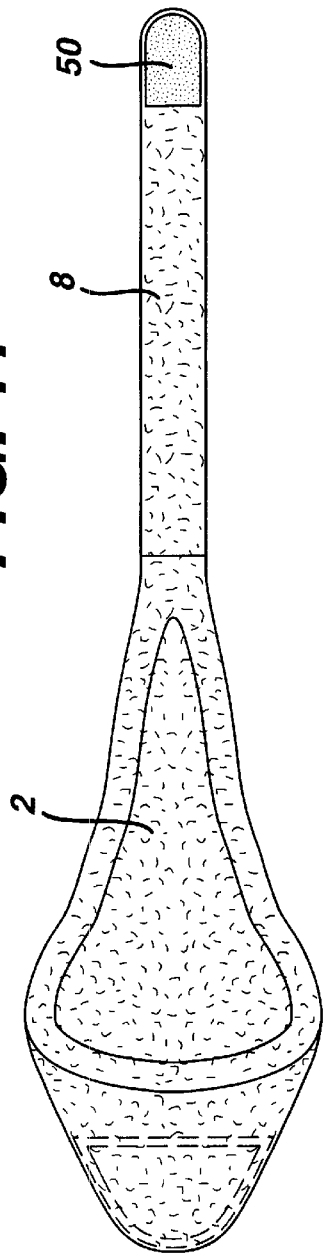

FIG. 12A  FIG. 12B
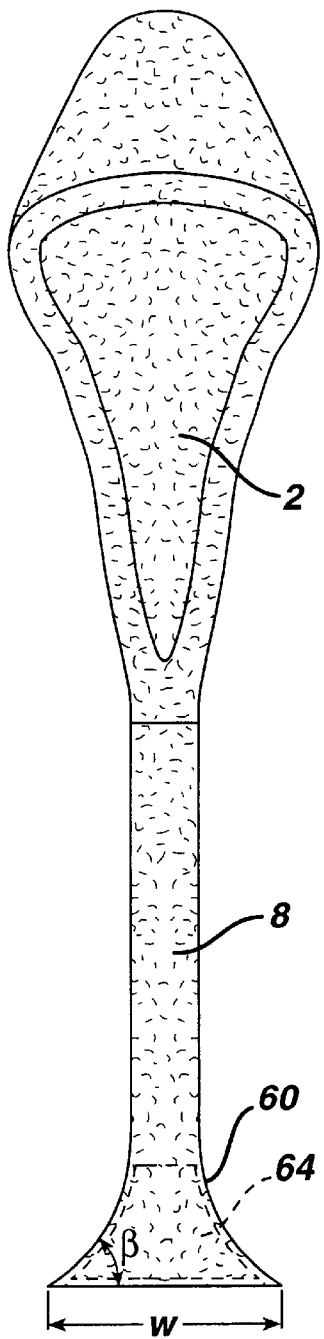
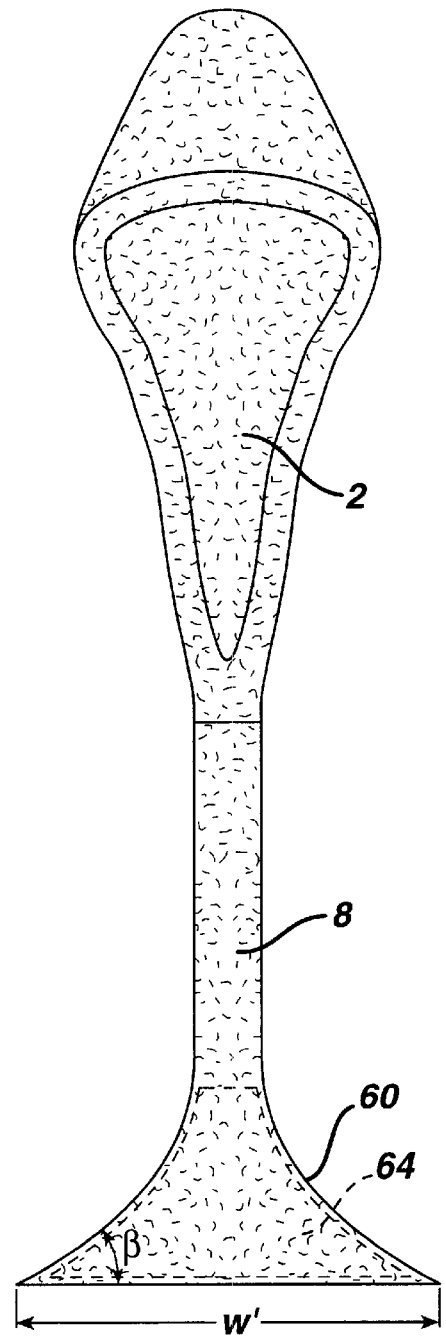

SANITARY NAPKIN WITH INTERGLUTEAL STRIP

FIELD OF THE INVENTION

The invention relates to a sanitary napkin having a strip of material that extends rearwardly to reside in the intergluteal crevice. This arrangement permits the pad portion of the napkin to fit more snugly against the body thereby providing improved protection.

BACKGROUND OF THE INVENTION

External sanitary protection is known to greatly depend upon the proximity of the napkin to the perineal area. A close fit allows the napkin to collect fluid near the source of the exit from the body and minimizes fluid traveling along the body. However, despite the importance of fit to sanitary protection, prior art napkins adhesively secured to the crotch of the garment rely on the relatively loose fit of the user's undergarments. Panties worn while menstruating are often older, well-worn garments which fit poorly. New panties, unless specially designed to do so, rarely hold and maintain the napkin close enough to be effective. Even specially designed undergarments are deemed by many women to be binding and uncomfortable.

In addition, reliance on adhesive systems that secure sanitary napkins to the garment essentially demand that the securing means of the napkin tenaciously adhere to the garment at all times. Accordingly, they must resist moisture, sudden torques generated by movements of the body and frictional shearing forces exerted by the movements of the various layers of clothing worn by the user. Not surprisingly, the actual performance of the napkin fails to satisfactorily meet these conditions.

One prior art solution to the fitting problem has been to use sanitary belts to independently support the napkin. Napkins with long tab ends worn with sanitary belts achieve the necessary closeness to the body but are often uncomfortable, inconvenient to use, and cause an indiscreet appearance which women find objectionable. Moreover, belts suspend a napkin in such a way that it is allowed to shift and twist, greatly reducing its effectiveness.

Another solution, contemplated by the prior art, is to attach the product ends to the skin. Several patents have been directed to devices for collecting body fluids that employ adhesive attachments to the skin. Zamist, U.S. Pat. No. 3,906,952, is directed to an anatomically contoured sanitary napkin having adhesive patches which attach to the skin of the wearer. These patches have non-disposable, die-cut grippers to receive the ends of the napkin. Levine, U.S. Pat. No. 4,072,151 describes a catamenial napkin having a long, full-sized napkin with adhesive strips on its longitudinal ends for attaching to the body. Sohn, U.S. Pat. No. 4,484,919, teaches a rectal area dressing for anal incontinence. This rectoperineal device has pressure-sensitive adhesive on an elongated absorbent pad and on extending end members that adhere to the skin surfaces.

While these inventions generally provide a close fit to the wearer's body, many women are adverse to the use of body adhesive. Further these prior art uses of adhesives do not permit stretching in the longitudinal direction to adjust to the wearer's individual sizing needs. Such devices, moreover, are not flexible enough to allow the pad to move with the body and return to its original position during stooping, bending and twisting. This can lead to uncomfortable binding and twisting of the napkin. Furthermore, the attachment sites of these products, being susceptible to sudden torques and shearing forces, are not always reliable in securing product placement.

The present invention relates to a sanitary napkin whose securing means comprises an intergluteal strip. While use of intergluteal pads has been disclosed in the prior art, their use has been for increased absorbency of fluids present in this area. Examples include U.S. Pat. No. 5,520,675 in the name of Knox-Sigh, U.S. Pat. No. 4,900,319 in the name of Richwine, PCT publication WO 90/04956 in the name of Muller, and U.S. Pat. No. Re. 24,385 in the name of Flanders.

The present invention relates to a sanitary napkin whose securing means comprises an intergluteal strip which thereby makes use of the wearer's intergluteal crevice to help secure the napkin. By using the wearer's body in this manner, the present invention reduces many of the sudden torques and shearing forces associated with the prior art. Further, it does so in a manner that does not require adhesive on that intergluteal strip portion. In addition it permits flexibility of the intergluteal strip. Consequently, an improved fit of the sanitary napkin is obtained.

SUMMARY OF THE INVENTION

The invention provides a sanitary napkin which achieves a dynamic body fit. The pad of the napkin is closely fit to the user's body by means that comprises an intergluteal strip. When the user moves, the user's panty may move, but the pad stays snugly against the body because of this attachment means.

More specifically, in accord with one aspect of the invention, there is provided a feminine hygiene pad comprising:

(a) a main pad body having an absorbent core system positioned between a pad cover material and a barrier layer, a rear end which in use is located in proximity to a wearer's buttocks and an opposed front end, a first face adapted to contact with the wearer's body and an opposing second face adapted to face toward an undergarment of the wearer, a main pad body thickness being defined as the dimension of the main pad body from the first face to the second face, said main pad body adapted to be worn in close proximity to the vagina of the wearer;

(b) said absorbent core system being adapted to not significantly extend beyond the anterior portion of the perineum of the wearer in use;

(c) said pad further comprising a substantially planar tail, said tail being relatively small thickness compared to the thickness of the main pad body, and said tail extending rearwardly from said rear end of the main pad body, terminating at a distal end; and, (d) wherein said pad being configured such that said tail is adapted to be received between the buttocks of the wearer to thereby facilitate retaining said main pad body adjacent to the wearer's vagina.

These and other features of the invention will be more fully understood by reference to the following drawings

BRIEF DESCRIPTION OF THE DRAWINGS

FIG. 1 is a top view of the inventive pad.

FIG. 2 is a cross sectional view of the pad of FIG. 1.

FIG. 8 is a top view of an alternative embodiment of the invention illustrating a dual front flap arrangement having a body-adhesive area on each front flap.

FIGS. 9A and 9B are bottom views of alternative embodiments of the invention in which a garment adhesive area is located on the main pad body.

FIG. 10 is a top view of an alternative embodiment of the invention illustrating a garment-adhesive area on the distal end of the tail for attachment to the rear of the user's panties.

FIG. 11 is a top view of an alternative embodiment of the invention illustrating a body adhesive area on the distal end of the tail for securing the tail to the user's body.

FIGS. 12A and 12B illustrate alternative embodiments of the invention in which a stabilizer area of the tail is depicted.

FIG. 13B further depicts the placement of the intergluteal tail in an embodiment of the invention wherein the tail does not contain a stabilizer area, while FIG. 13C depicts the placement of the intergluteal tail in an embodiment in which a stabilizer area is present.

DETAILED DESCRIPTION OF THE INVENTION

Figure 3:
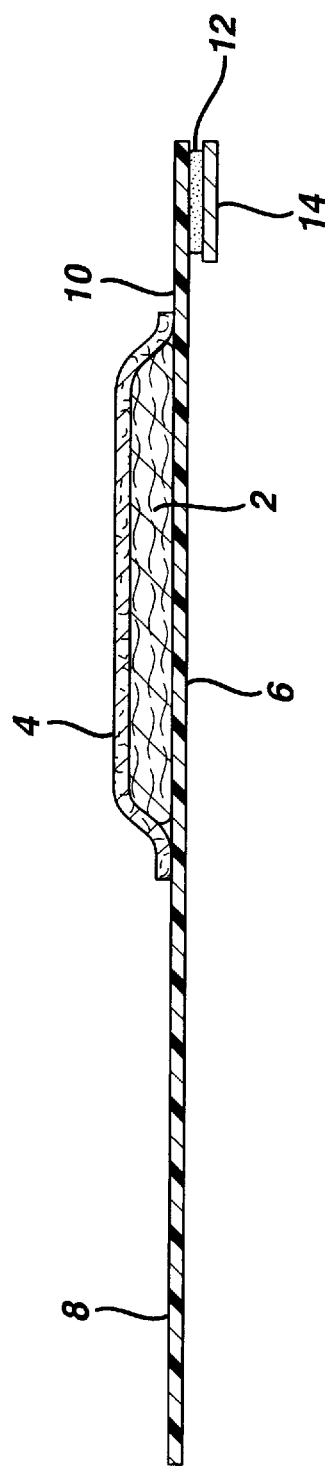
FIG. 3 is a cross sectional view of an alternative embodiment of the invention illustrating the barrier material forming the tail and flap.

During the course of this description, like numbers will be used to identify like elements according to different figures which illustrate the invention.

FIG. 1 shows an embodiment of the present invention and FIG. 2 shows a corresponding cross-sectional view. The depicted sanitary napkin 1 has a central longitudinal axis 16. As depicted in these FIGS., the main pad body 17 of this sanitary napkin 1 extends from point P₂ to point P₃ on the longitudinal axis 16 and comprises an absorbent core system 2 positioned between a pad cover material 4 and a barrier layer 6. This main pad body has a front end 18 located adjacent to point P₃ and a rear end 19 located adjacent to point P₂. In the embodiment shown the cover 4 and barrier 6 are slightly larger than the absorbent system, leaving room to heat seal along the perimeter of the pad.

In the depicted embodiment the intergluteal tail 8 is connected to the main pad body and is placed underneath the absorbent core system so as not to interfere with absorbency. Construction adhesives as well as heat are exemplary means to attach the tail 8 to the main pad body. In the preferred embodiment the tail is composed of a polyester knit fabric such as that manufactured by Tomen Corporation under the designation AQ 7500. An alternative embodiment the tail may be composed of a nonwoven material which has been microcreped, an example of which being the microcreped material available from Micrex corporation. Use of such a microcreped material allows the material to expand in use to accommodate the user's body. The invention is not limited to these material as alternative materials, to include stretchable or absorbent materials, are contemplated by the inventors.

Moreover, the invention is not limited to positioning of the intergluteal tail between the cover material 4 and the barrier layer 6. An alternative embodiment depicted in FIG. 3 has the barrier layer material itself extended to form both the tail and the optional front flap 10. Alternative embodiments would be having the barrier layer extending to form only one of these appendages while the remaining appendage being an attached material. Accordingly, the materials used in the construction of the tail and or the optional front flap could be selected to best match the desired physical characteristics (e.g. elasticity, absorbency, etc.), to minimize cost, or to simplify construction.

Alternative embodiments (not shown) of the sanitary napkin would comprise the presence of channeling or embossing on the cover material. Such channeling is well known in the sanitary napkin industry.

Figure 4:
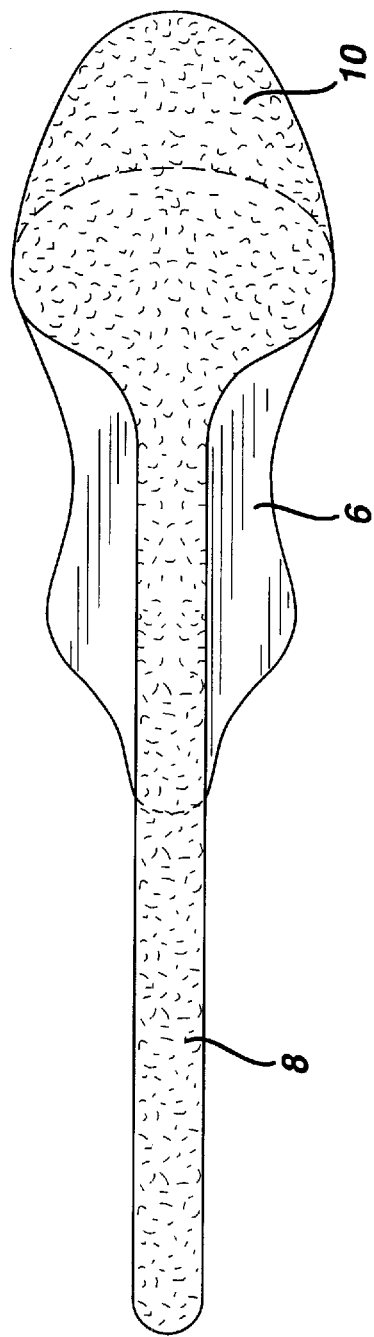
FIG. 4 is a bottom view of another alternative embodiment in which a continuous piece of material which forms the tail and flap is attached to the barrier layer.

FIG. 4 shows the garment facing side of an additional alternative embodiment of the invention in which the intergluteal tail 8 and the front flap are one continuous piece of material that has been attached to the barrier layer 6. Construction adhesives as well as heat are exemplary attachment means. In this embodiment construction of the pad is simplified while not limiting the barrier layer to be of the same material as both appendages.

As depicted in FIG. 2 the optional front flap 10, located at the front end 18 of the main pad body 17, comprises positioning adhesive 12 and release paper 14 on the garment-facing side. In the preferred embodiment depicted in FIGS. 1 and 2, the front flap is sandwiched between the cover 4 and barrier 6, and is attached using construction adhesive as well as heat. In this preferred embodiment it is envisioned that this front flap is constructed of a stretchable material to aid in both comfort and fit of the pad.

Figure 5:
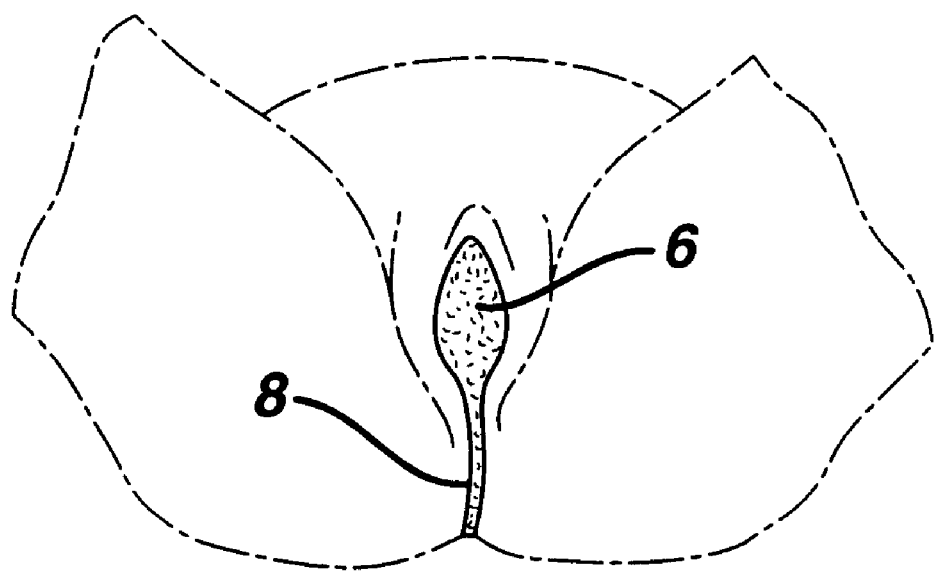
FIG. 5 is a front view of the inventive pad as worn by a wearer.

As illustrated in FIG. 5 the intergluteal tail extends rearwardly into the area of space between the buttocks of the wearer. The placement of the intergluteal tail in this position thus provides an additional anchoring means for the pad. An important feature of the present invention is that in use, the absorbent core system 2 of the pad does not extend significantly beyond the anterior portion of the user's perineum. As is well known, the perineum of a user is defined to be that area that extends between the anus and the posterior part of the external genitalia. Consequently, in normal use the absorbent core system of the pad does not rearwardly extend significantly beyond the user's anus, and accordingly extends minimally, if at all, into the intergluteal crevice of the user. Preferably, when the pad is worn, the absorbent core system extends less than 25 mm beyond the anterior portion of the user's perineum; and most preferably does not extend beyond the anterior portion of the user's perineum.

In the preferred embodiment of the present invention the sanitary pad of the present invention provides dynamic fit by anchoring the front end of the pad to the body through the use of just one attachment point to the panty. The pad is draped closely to the body through the use of the intergluteal tail. Once in place, the pad moves with the body, not with the panty. Hence, dynamic fit is achieved. Because of this optimal fit, the user can achieve the same protection in a smaller, more discreet pad.

Figure 6:
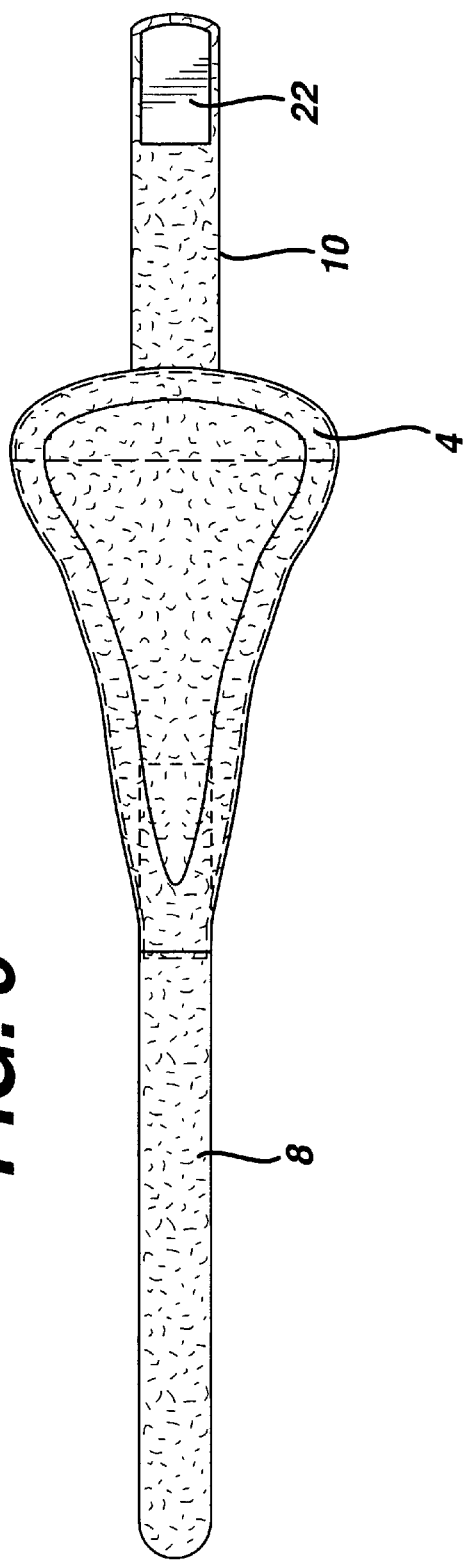
FIG. 6 is a top view of an alternative embodiment of the invention illustrating a body-adhesive area on the front flap.
Figure 7:
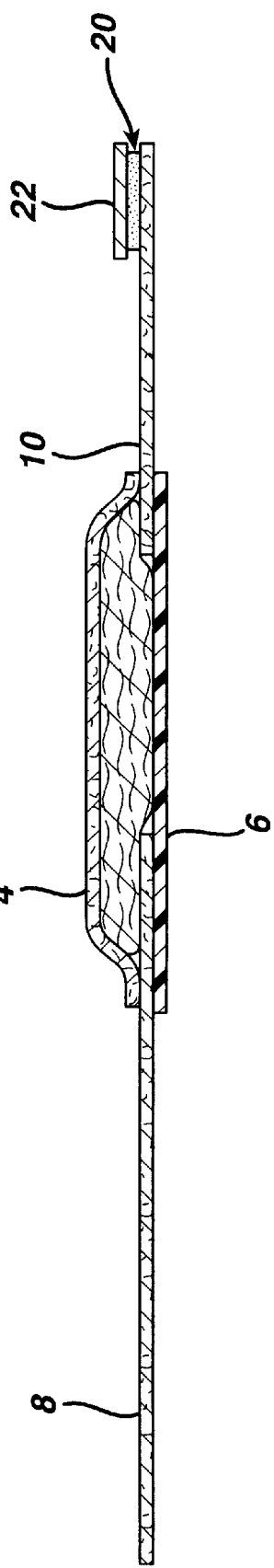
FIG. 7 is a cross sectional view of the pad of FIG. 6.

Alternative embodiments utilize a body adhesive to secure the front end of the pad without the necessity of attaching it to the user's panty. One such embodiment is depicted in FIGS. 6 and 7 and wherein the front flap 10 is of sufficient length such that when worn, the body adhesive area 20 of the flap extends above and hence is not in contact with the pubic hair area of the user. As depicted in FIG. 7 this adhesive area is covered by release paper 22 prior to its use. An alternative embodiment of this aspect of the invention is depicted in FIG. 8 in which two front flaps are utilized to form the pad into a "Y" shape. Consequently when worn, the ends of the flaps extend both up and away from the user's crotch area to avoid contact of the body adhesive with pubic hair area.

FIG. 9A depicts yet another alternative pad in which the body of the pad is secured to the user's undergarment by use of a position adhesive area 30 on the barrier layer and hence on the garment facing side of the pad. Consequently, the front flap is not required.

An alternative use of garment adhesive is shown in FIG. 9B. This figure depicts a smaller position adhesive area 30 that is located near the tail. This adhesive area is used chiefly to help properly position the pad in the wearer's undergarment just prior to use. Once the undergarment is pulled up into a wearing position and the tail 8 is placed in the intergluteal crevice; it is contemplated that this adhesive area would no longer secure the pad to the user's undergarment.

In the preferred embodiment, the tail lacks any presence of adhesive on its distal end. As illustrated in FIG. 5 the intergluteal tail is placed by the wearer in her intergluteal crevice. This positioning of the tail into this area is sufficient to secure the tail end of the pad. Alternative embodiments are contemplated in which the intergluteal tail is of sufficient length to employ an adhesive on its distal end. As depicted in FIG. 10 this adhesive area 40 may be positioned on the garment facing side for attachment to the user's undergarment. Alternatively a body adhesive area 50 on the body facing side could be employed for securing the distal end of the tail as depicted in FIG. 11. A napkin containing such adhesive areas would preferably utilize an adhesive release paper to facilitate packaging and handling of the napkin prior to its use.

In the following discussion length measures correspond to distances along the central longitudinal axis 16 of the pad as depicted in FIG. 1. Width measures relate to distances along a corresponding horizontal axis perpendicular to this longitudinal axis. Accordingly, the length of the intergluteal tail 8 is the distance from point $P_1$ to point $P_2$ along longitudinal axis 16. Similarly, the main body of the pad extends in length from point $P_2$ to point $P_3$ along this axis. And finally, the length of the front flap is the measure from point $P_3$ to point $P_4$.

In the preferred embodiment the front flap has a rounded shape that flows from the contours of the main pad body as depicted in FIG. 1. Its width varies along the length of the flap. The widest portion is adjacent to the main pad body and the narrowest portion is at the distal end, ending in a rounded point. The widest portion has a width of 7 cm, but can vary with the width of the main pad body, from 7 to 10 cm. The length of the flap extends 4 cm beyond the end of the main pad body. The length of the flap can range from 3 to 7 cm.

The tail extends 15 cm from the rear end 19 of the main pad body. A range in length from 10 to 30 cm would be acceptable. Preferably, the tail's length ranges from 12 to 18 cm. The width of the tail can vary from 0.5 to 2.5 cm. Preferably, the tail has a width of 1.5 to 2 cm. The thickness of the tail is preferable less than 1 cm and most preferably less than 5 mm. This thickness range is an important feature of the present invention as it relates to the user's comfort. The distal end of the intergluteal tail can have adhesive in a range of patterns, including full coverage of the tail contour, strips, dots, or other.

In the preferred embodiment the main body of the pad is adapted to be worn outside of and in close proximity to the vagina of a wearer. Accordingly, in this embodiment the main pad body is substantially planar on its body facing side. Additional embodiments, while also substantially planar, have some taper in a front to back direction, or in a side to side direction, or both. However, the invention is not limited to being worn outside of the vagina. Additional alternative embodiments are contemplated in which the main pad body comprises a raised area for insertion into the vagina. Such an interlabial feature yields several advantages to include aiding in proper positioning of the pad and/or permitting a concentration of absorbent materials at the fluid discharge location.

In the preferred embodiment of the present invention, the absorbent core system is of sufficient length to only cover the length of the user's labia, that is, it is in the range 8.0 to 13.1 cm in length. The length of the main pad body is preferably greater than the length of the absorbent core system 2, so that a perimeter of barrier layer 6 and cover material 4 surrounds the absorbent core. The width of the perimeter can range from 0.5 to 2 cm. This means the length of the main pad body can range from 9.0 to 17.1 cm. Most preferably, the width of the perimeter is 1 cm. With a most preferred length of absorbent body of 11.5 cm, this means that the most preferable length of the main pad body is 13.5 cm.

The width of the main pad body most preferably varies along the length, becoming narrower at the rear end 19 of the main pad body. It could be relatively constant in width as well. In the preferred embodiment with a variable width, the maximum width occurs near the front end 18. The width there is in the range 8 cm to 10 cm. In the preferred embodiment, the main pad body is most narrow, at the rear end 19 near the tail to thereby provide a more comfortable fit. Accordingly, this width is preferably between 0.5 and 4 cm. Most preferably, this width is 2 cm. Further, in the preferred embodiment the narrowest part of the main pad body should approximately equal the width of the intergluteal tail 8, which can vary from 0.5 to 2.5 cm.

In accordance with alternative embodiments the present invention relates to full size napkins wherein the main pad body has a length of 200 cm to 250 cm and overnight napkins whose main pad body has a length of 250 cm to 350 cm. In addition, alternative embodiments are contemplated in which the napkin has one or more wings extending from each lateral side of the main pad body, these wings to be used to further secure the napkin to the user's undergarments. Such wings are well known in the sanitary napkin industry.

Additional embodiments of invention relate to a widened distal end of the tail thereby forming a stabilizer area 60 of the tail. FIGS. 12A and 12B depict alternative embodiments of this invention in which the width (w and w', respectively) of the stabilizer area 60 is greater than the width of the intergluteal tail 8. This arrangement helps stabilize the tail by providing a larger attachment area that distributes the forces acting upon the tail by spreading them laterally. As illustrated in these figures, both the width of the stabilizer portion, and the angle of stabilization, β, combine to determine the surface area of the stabilizer area 60.

This stabilizing area may contain an area of adhesive 64. In the preferred embodiment this adhesive would be covered by a release paper (not shown) prior to use. In FIG. 12 panty adhesive is depicted on the garment facing side of the tail. In the preferred embodiment body adhesive, for directly attaching the tail to the user's body, would be utilized. Moreover, while FIGS. 12A and 12B illustrate the adhesive area essentially taking the same shape as the stabilizing area, this is not required. Any number of adhesive pattern area shapes, including but not limited to, square, rectangular, circular, or even linear are contemplated by the invention.

Figure 13A:
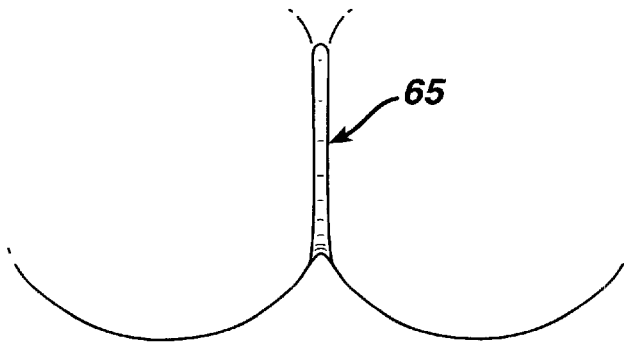
FIGS. 13A, 13B and 13C depict a rear view of a user's buttocks and the intergluteal crevice therein.
Figure 13B:
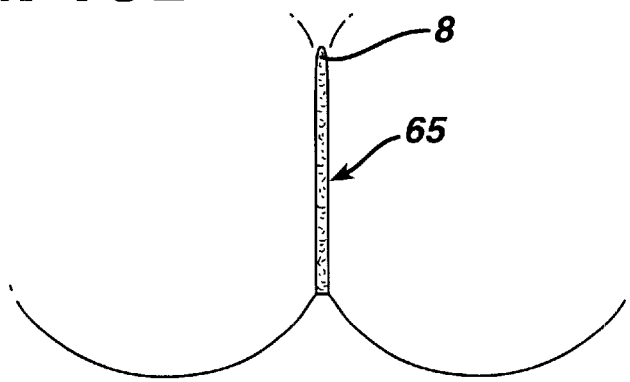
Figure 13C:
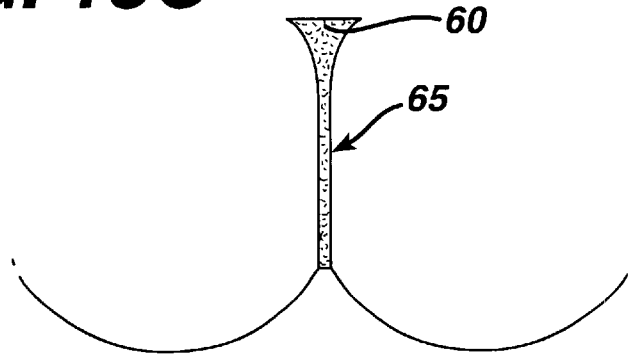

FIGS. 13A, B and C each depict a rear view of a user's buttocks. FIG. 13A illustrates the user's intergluteal crevice 65. FIG. 13B depicts an intergluteal tail 8, which lacks a stabilizing area, positioned in the intergluteal crevice 65. FIG. 13C illustrates a user wearing an intergluteal tail 8 having a stabilizing area 60. Such a stabilizing area not only stabilizes the forces acting upon the tail, but also helps prevent the tail from residing too far in the intergluteal crevice, a situation which users may find uncomfortable.

FIG. 13C further illustrates how the width of the stabilizer area, W, and the angle of stabilization, β, combine to effect the surface area of the stabilizer area. The lower limits of these parameters are influenced by the stability of the material used. The upper limits of these parameters are influenced by discretion since, as illustrated in FIG. 13C, the stabilizer area resides outside of the intergluteal crevice when the tail is in position. In the preferred embodiment the angle of stabilization, β, can range from 5° to 80°. While for a 20 mm wide tail, the preferred range of w is from 30 to 120 mm.

Figure 14:
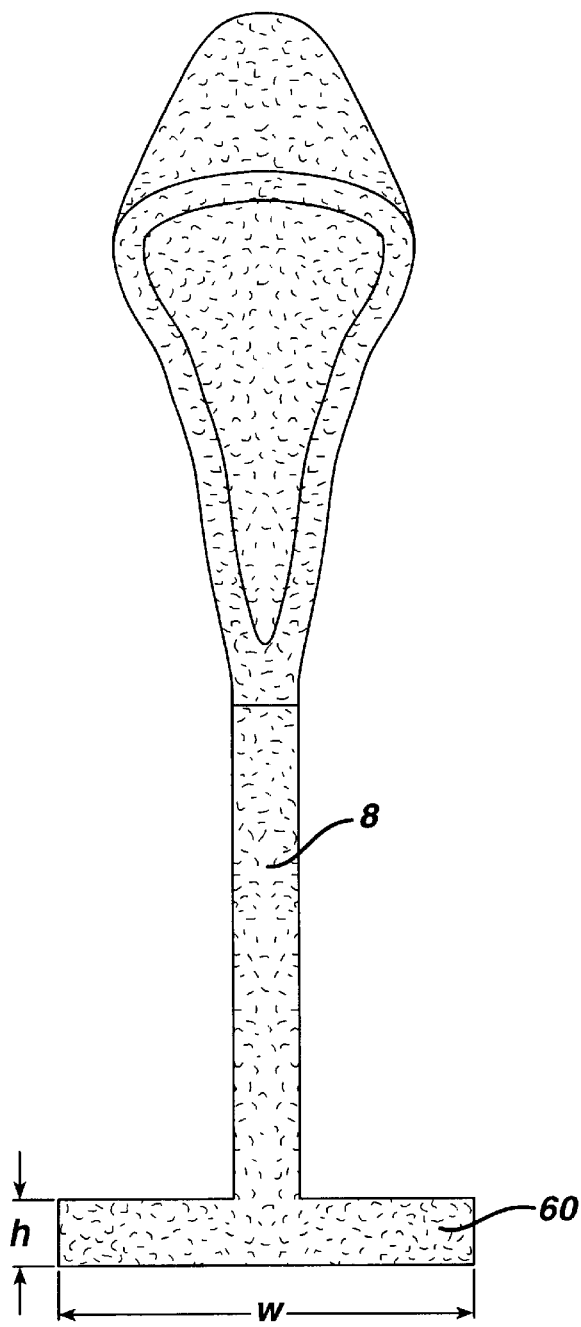
FIGS. 14 and 15 depict alternative embodiments of the invention wherein the stabilizer area has alternative shapes.
Figure 15:
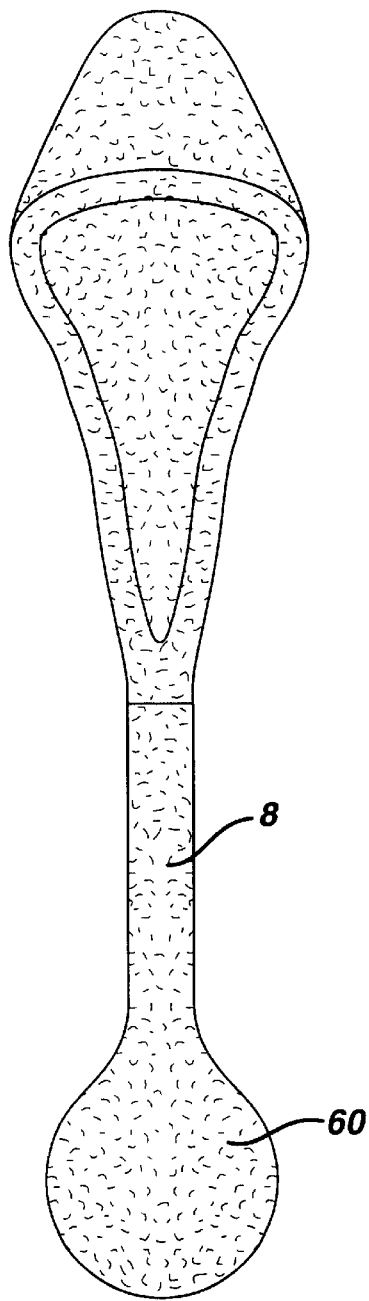

FIG. 14 depicts an alternative embodiment of the stabilizer area 60. In this embodiment, the height, h, preferentially ranges from 6 mm to 40 mm and for a 20 mm wide tail, the width, w, preferentially ranges from 30 to 120 mm. FIG. 15 depicts yet another alternative embodiment of the shape of the stabilizer area 60. The invention is not limited to these illustrated shapes as any non-insignificant widening of the distal end of the intergluteal tail 8 will perform as a stabilization area and help prevent the tail from residing too far in the intergluteal crevice.

Further, in situations in which an adhesive is desired at the distal end of the intergluteal tail, this stabilizing area provides an increased surface area upon which such adhesive can be placed. Finally, the stabilization area provides a convenient tab to aid the wearer in the placement of the tail at time of use.

The above discussion of the stabilization area relates primarily to that area being a widening of the tail material at the distal end of the tail. The invention is not limited in this regard as it is contemplated that a separate stabilizing strip of material can be attached to the distal end of the intergluteal tail to thereby form the stabilization area. In the preferred embodiment this stabilizing strip would be readily stretchable. Non-limiting examples of suitable materials include: LYCRA XA Q-3, a laminate of two layers of low basis weight spunbond PP sandwiching lycra strands, which is manufactured by the DuPont Corporation; AQ 3005, a polyester/polyurethane knit laminate, and AQ 7500, a polyester knit fabric, both commercially available from the Tomen Corporation; FABRIFLEX 102, a laminate of PP nonwoven and a high stretch elastic film, manufactured by Tredagar Corporation; and a cotton/rayon bandage material, with the yarns mechanically twisted to provide stretch available from Conco under the trade designation ARTICLE 207.

An additional alternative embodiment of the invention is that the tail comprise a gentle body adhesive along at least part of its length. Use of such an adhesive helps to secure the tail (and thereby the pad) in place. In addition, the use of such an adhesive helps to form an impervious gasket thereby minimizing any potential leakage from occurring towards the posterior of the wearer. Examples of such adhesives include, but are not limited to, hydrogel adhesives, TPE/Oil gel adhesives, and polyethelyene glycolpolyacrylate adhesives.

While the invention has been described with reference to the above alternative embodiments thereof, it will be appreciated by those of ordinary skill in the art that various modifications can be made to the structure and function of the individual parts of the system without departing from the spirit and scope of the invention as a whole.

We claim:

1. A feminine hygiene pad comprising:
   a main pad body having an absorbent core system positioned between a pad cover material and a barrier layer, a rear end which in use is located in proximity to a wearer's buttocks and an opposed front end, a first face adapted to contact with the wearer's body and an opposing second face adapted to face toward an undergarment of the wearer, a main pad body thickness being defined as the dimension of the main pad body from the first face to the second face, said main pad body adapted to be worn in close proximity to the vagina of the wearer;

said absorbent core system being adapted to not significantly extend beyond the anterior portion of the perineum of the wearer in use;

said pad further comprising a substantially planar tail, said tail being relatively small in thickness compared to the thickness of the main pad body, and said tail extending rearwardly from said rear end of the main pad body, terminating at a distal end; and, wherein said pad being configured such that said tail is adapted to be received between the buttocks of the wearer to thereby facilitate retaining said main pad body adjacent to the wearer's vagina wherein said pad further comprises a front flap, extending forwardly from the front end of the main pad body and terminating at a distal end, said flap adapted to aid in retaining said main pad body adjacent to the wearer's vagina.

2. A pad as recited in claim 1, wherein said front flap is stretchable.

3. A pad as recited in claim 1, wherein said distal end of said front flap contains an area of adhesive adapted for attaching said distal end to said undergarment of the wearer.

4. A pad as recited in claim 1, wherein said front flap contains an area of body adhesive adapted for attaching said distal end to the wearer's body.

5. A pad as recited in claim 4, comprising an additional front flap extending forwardly from the main pad body and containing an area of body adhesive adapted for attaching to the wearer's body, wherein said front flap and said additional front flap are attached to the main pad body in a "Y-shaped" configuration.

6. A pad as recited in claim 4, wherein said opposing second face comprises an area of adhesive for use in positioning the main pad body in the wearer's underwear.

7. A pad as recited in claim 1, wherein both said front flap and said tail are connected to the main pad body in a position between the absorbent core system and the barrier layer.

8. A pad as recited in claim 1, wherein the front flap, the tail or both the front flap and tail are formed by extending the barrier layer.

9. A pad as recited in claim 1, wherein both said front flap and said tail are formed from one continuous piece of material that has been attached to said second face of the main pad body.

10. A pad as recited in claim 1, wherein said main pad body is substantially planar.

11. A pad as recited in claim 10, wherein said main pad body has a central region that is substantially planar which tapers towards its edges.

12. A pad as recited in claim 1, wherein said tail is flexible.

13. A pad as recited in claim 1, wherein said tail is stretchable.

14. A pad as recited in claim 1, wherein said tail comprises an absorbent material.

15. A pad as recited in claim 1, wherein said tail is nonabsorbent.

16. A pad as recited in claim 1, wherein said tail is adjustable in length.

17. A pad as recited in claim 1, wherein said tail comprises an area of adhesive at its distal end, said adhesive adapted to secure said tail to the wearer's undergarment.

18. A pad as recited in claim 1, wherein said tail comprises an area of adhesive at its distal end, said adhesive adapted to secure said tail to the wearer's body.

19. A pad as recited in claim 1, wherein said tail comprises a region of body adhesive along its length.

* * * * *

UNITED STATES PATENT AND TRADEMARK OFFICE
CERTIFICATE OF CORRECTION

PATENT NO. : 6,632,210 B1
DATED : October 14, 2003
INVENTOR(S) : Tara Glasgow et al.

It is certified that error appears in the above-identified patent and that said Letters Patent is hereby corrected as shown below:

<u>Title page,</u>
Item [73], Assignee, should be -- McNeil-PPC, Inc. --

Signed and Sealed this

Twentieth Day of January, 2004

JON W. DUDAS
*Acting Director of the United States Patent and Trademark Office*